US006299875B1

(12) United States Patent
Caplan et al.

(10) Patent No.: US 6,299,875 B1
(45) Date of Patent: Oct. 9, 2001

(54) METHODS TO BLOCK IGE BINDING TO CELL SURFACE RECEPTORS OF MAST CELLS

(75) Inventors: Michael Caplan, Woodbridge; Howard Sosin, Fairfield, both of CT (US)

(73) Assignee: Panacea Pharmaceuticals, LLC, Fairfield, CT (US)

( * ) Notice: Subject to any disclaimer, the term of this patent is extended or adjusted under 35 U.S.C. 154(b) by 0 days.

(21) Appl. No.: 09/090,375

(22) Filed: Jun. 4, 1998

(51) Int. Cl.$^7$ .................. A61K 39/395; A61K 38/02; C07K 16/28

(52) U.S. Cl. .................. 424/133.1; 424/143.1; 424/151.1; 424/805; 424/810; 514/21; 530/388.22; 530/388.6; 530/862; 530/866

(58) Field of Search ................ 424/133.1, 143.1, 424/151.1, 805, 810; 514/21; 530/388.22, 388.6, 862, 866

(56) References Cited

U.S. PATENT DOCUMENTS

| | | |
|---|---|---|
| 3,625,214 | 12/1971 | Higuchi et al. . |
| 4,244,946 | 1/1981 | Rivier et al. . |
| 4,305,872 | 12/1981 | Johnston et al. . |
| 4,316,891 | 2/1982 | Guillemin et al. . |
| 4,629,784 | 12/1986 | Stammer . |
| 4,789,734 | 12/1988 | Ruoslahti et al. . |
| 4,792,525 | 12/1988 | Ruoslahti et al. . |
| 4,906,474 | 3/1990 | Langer et al. . |
| 4,925,673 | 5/1990 | Steiner et al. . |
| 5,612,895 | 3/1997 | Balaji et al. . |
| 5,770,396 * | 6/1998 | Kinet .................. 435/69.1 |

FOREIGN PATENT DOCUMENTS

| | | |
|---|---|---|
| 0 499 112 A1 | 8/1992 | (EP) . |
| WO 93/04173 A1 | 3/1993 | (WO) . |
| WO 95/14779 A1 | 6/1995 | (WO) . |
| WO 96/12741 A1 | 5/1996 | (WO) . |
| WO 97/04807 A1 | 3/1997 | (WO) . |

OTHER PUBLICATIONS

Kitani, S, et al., Inhibition of allergic reactions with monoclonal antibody to the high affinity IgE receptor. J. Immunol. 140(8):2585–2588, Apr. 15, 1988.*

Allen, F. H., et al., "The Cambridge Crystallographic Data Centre: Computer–Based Search, Retrieval, Analysis and Display of Information," *Acta Crystallogr.*, B35: 2331–2339, (1979).

Baniyash, et al. "Anti–IgE Monoclonal Antibodies Directed at the Fc, Receptor Binding Site," *Molec. Immunol.* 25:705–711, (1988).

Bonini, et al. "HSV–TK Gene Transfer into Donor Lymphocytes for Control of Allogenic Graft–Versus–Leukemia," *Science* 276: 1719–1724, (1997).

Brent, et al., "Upperbound Procedures for the Identification of Similar Three–Dimensional Chemical Structures," *J. Comput.–Aided Mol. Design*, 2: 311–310, (1988).

Burt, et al., "Analysis of the Interaction Between Rat Immunoglobulin E and Rat Mast Cells Using Anti–Peptide Antibodies," *Molec. Immunol.* 24: 379–389, (1987).

Clackson, T., et al., "Making Antibody Fragments Using Phage Display Libraries," *Nature*, 352:624–688, (1991).

Coleman, et al., "Inhibition of Mast Cell Sensitization in vitro by a Human Immunoglobulin ,–chain Fragment Synthesized in *Escherichia coli*,*" *Eur. J. Immunol.* 15:966–969, (1985).

Cooper, et al., "A Novel Approach to Molecular Similarity," *J. Comput.–Aided Mol. Design*, 3: 253–259 (1989) and references cited therein.

Daugherty, et al., "Polymerase Chain Reaction Facilitates the Cloning, CDR–Grafting, and Rapid Expression of a Murine Monoclonal Antibody Directed Against the CD18 Component of Leukocyte Integrins," *Nucl. Acids Res.*, 19:2471–2476 (1991).

Durham, et al., "Expression of , Germ–Line Gene Transcripts and mRNA for the , Heavy Chain of IgE in Nasal B Cells and the Effects of Topical Corticosteriod," *Eur. J. Immunol.* 27: 2899–2906, (1997).

Durham, et al., "Local IgE Production in Nasal Allergy," *Int. Arch. of Allergy and Immunol.* 113: 128–130, (1997).

Ellington & Szostak, "In Vitro Selection of RNA Molecules that Bind Specific Ligands," *Nature* 346:818–822, (1990).

Ellington & Szostak, "Selection in vitro of Single–Stranded DNA Molecules that Fold into Specific Ligand–Binding Structures," *Nature* 355:850–852, Feb., (1992).

(List continued on next page.)

*Primary Examiner*—David Saunders
*Assistant Examiner*—Mary Beth Tung
(74) *Attorney, Agent, or Firm*—Choate, Hall & Stewart; Brenda Herschbach Jarrell

(57) ABSTRACT

Compositions are administered to block IgE binding to receptors and ultimately displace native IgE from mast cells and related cell types, to prevent the activation of these cells during an allergic response. The compositions consist of a pharmaceutically acceptable carrier for systemic or local administration and an amount of compound binding specifically to the FcεRI IgE binding sites, and more preferably, FcεRI and FcεRII IgE binding sites, to prevent activation and degranulation of mast cells in response to exposure to allergens. The compounds can consist of IgE molecules and fragments and modifications thereof, such as IgE fragments, humanized or single chain IgE antibodies or fragments thereof, IgE with a modified Fab, non-crosslinkable IgE, or peptidomimetics which bind to the same site on the receptor as the IgE, jointly referred to herein as "IgE fragments" unless otherwise stated.

11 Claims, No Drawings

OTHER PUBLICATIONS

Elliot, et al., "Parenteral Absorption of Insulin from the Lung in Diabetic Children," *Aust. Paediatr. J.* 23: 293–297, (1987).

Geha, et al., "Inhibition of the Prausnitz–Kηstner Reaction by an Immunoglobulin ,–Chain Fragment Synthesized in *E. coli,*" *Nature.* 315:577–578, (1985).

Bensch, et al., "Absorption of Intact Protein Molecules across the Pulmonary Air–Tissue Barrier," *Science* 157:1204–10206, (1967).

Ghoshal et al., "Computer Aids in Drug Design—Highlights" *Pol. J. Pharmacol.* 48(4), 359–377, (1996).

Helm, et al., "Identification of the High Affinity Receptor Binding Region in Human Immunoglobulin E*," *J. Biol. Chem.* 271: 7494–7500, (1996).

Helm, et al., "The Mast Cell Binding Site on Human Immunoglobulin E," *Nature* 331: 180–183, (1988).

Helm, et al., "Blocking of Passive Sensitization of Human Mast Cells and Basophil Granulocytes with IgE Antibodies by a Recombinant Human ,–Chain Fragment of 76 Amino Acids," *Proc. Nat. Acad. Sci.* 86:9465–9469, (1989).

Huang et al., "Development of a Common 3D Pharmacophore for Delta–Opioid Recognition From Peptides and Non–Peptides Using a Novel Computer program" *J. Comput. Aided Mol. Des.* 11(1): 21–78, (1997).

Ikeyama, "Purification and Characterization of Recombinant Human IgE Fc, Fragment Produced in Mouse L Cells," Molec. Immunol. 24: 1039–1046, (1987).

Isersky, et al., "The Fate of IgE Bound to Rat Basophilic Leukemia Cells," *J. Immunol.* 122: 1926–1936, (1979).

Ishizaka, et al., "Biological Properties of a Recombinant Human Immunoglobulin ,–Chain Fragment," *Proc. Nat. Acad. Sci.* 83:8323–8327, (1986).

Kamiya, "Unsusceptibility of Recombinant Human Fc Fragments of Immunoglobulin E to Thrombin," *Human Antibodies and Hybridomas* 7:42–47, (1996).

Keegan, et al., "Characterization of New Rat Anti–Mouse IgE Monoclonals and Their Use Along With Chimeric IgE to Further Define the Site that Interacts with Fc,RII and Fc,RI," *Molec. Immunol.* 28: 1149–1154, (1991).

Kenten, et al., "Properties of a Human Immunoglobulin Chain Fragment Synthesized in *Escherichia coli,*" *Proc. Nat. Acad. Sci.* 81:2955–2959, (1984).

Keown, et al., "Basis of the 1:1 Stoichiometry of the High Affinity Receptor Fc,RI–IgE Complex," *Eur. Biophys J.* 25: 471–476, (1997).

Kleinberg and Wanke, "New Approaches and Technologies in Drug Design and Discovery," *Am. J. Health Syst. Pharm.* 52(12): 1323–1336, (1995).

Kubinyi, "Strategies and Recent Technologies in Drug Discovery" *Pharmazie* 50(10): 647–662, (1995).

Kurokawa, et al., "Expression of Human Immunoglobulin E Chain cDNA in *E. coli,*" *Nucleic Acids Res.* 11:3077–3085, (1983).

Li et al., "A Computer Screening Approach to Immunoglobulin Superfamily Structures and Interactions: Discovery of Small Non–Peptidic CD4 Inhibitors and Novel Immunotherapeutics" *Proc. Natl. Acad. Sci. USA* 94(1): 73–78, (1997).

Lybrand, "Ligand–Protein Docking and Rational Drug Design" *Curr. Opin. Struct. Biol.* 5(2): 224–228, (1995).

Merrifield, J., "Solid Phase Peptide Synthesis. I. The Synthesis of a Tetrapeptide," *J. Am. Chem. Soc.* 85, 2149, (1964).

Miller, et al., "Expression of Factor VII by Muscle Cells in vitro and in vivo Following Direct Gene Transfer: Modelling Gene Therapy for Haemophilia," *Gene Therapy* 2: 736–742, (1995).

Moscoso del Prado, et al., "Monoclonal Antibodies Against Human IgE. Identification of an Epitope Sharing Properties with the High–Affinity Receptor Binding Site," *Molec. Immunol.* 28: 839–844, (1991).

Nissim, A. and Z., "The Human Mast Cell Receptor Binding Site Maps to the Third Constant Domain of Immunoglobulin E," Eshhar. *Molec. Immunol.* 29:1065–1072, (1992).

Nissim, et al., "Mapping of the High Affinity Fc, Receptor Binding Site to the Third Constant Region Domain of IgE," *EMBO J.* 10:101–109, (1991).

Nissim, et al., "Fine Specificity of the IgE Interaction with the Low and High Affinity Fc Receptor," *J. Immunol.* 150: 1365–1374, (1993).

Nye, et al., "A Detailed Investigation of Circulating IgE Levels in a Normal Population," *Clin. Allergy* 1:13–24; (1975).

Patton, et al., "Absorption of Human Growth Hormone from the Rat Lung," *Biotech. Therap.* 1:213–228, (1990).

Perez–Montfort, R. and H. Metzger, "Proteolysis of Soluble IgE–Receptor Complexes: Localization of Sites on IgE Which Interact with the Fc Receptor," *Molec. Immunol.* 19:1113–1125, (1982).

Rousseaux–Prevost, et al., "Studies of the IgE Binding Sites to Rat Mast Cell Receptor with Proteolytic Fragments and with a Monoclonal Antibody Directed Against Epsilon Heavy Chain: Evidence that the Combining Sites are Located in the C, Domain," *Molec. Immunol.* 24: 187–196, (1987).

Spiegelberg, et al., "Effect of Myeloma IgE Injections on Passive and Active Cutaneous Anaphylaxis in Rats," *J. Immunol.* 136:131–135, (1986).

Szelke et al., In Peptides: Structure and Function, Proceedings of the Eighth American Peptide Symposium, (Hruby and Rich, Eds.); pp. 579–582, Pierce Chemical Co., Rockford, Ill. (1983).

Szostak, "In Vitro Genetics," *TIBS* 19:89, (1992).

Taylor and Smith, "The Word Wide Web as a Graphical User Interface to Program Macros for Molecular Graphics, Molecular Modeling, and Structure–Based Drug Design" *J. Mol. Graph.* 14(5): 291–296, (1996).

Tsien, et al., "Subregion– and Cell Type–Restricted Gene Knockout in Mouse Brain," *Cell* 87:1317–1326, (1996).

Vercelli, et al., "The B–Cell Binding Site on Human Immunoglobulin E," *Nature* 338:649–651, (1989).

Vrtala, et al., "Humoral Immune Responses to Recombinant Tree Pollen Allergens (Bet v I and Bet v II) in Mice: Construction of a Live Oral Allergy Vaccine," *Int. Arch. Allergy Immunol.* 107(1–3), 290–294 (1995).

Weetall, et al., "Mapping the Site of Interaction Between Murine IgE and Its High Affinity Receptor with Chimeric Ig," *J. Immunol.* 145: 3849–3854, (1990).

Weiner, et al., "A New Force for Molecular Mechnical Simulation of Nucleic Acids and Proteins," *J. Am. Chem. Soc.*, 106(3): 765–84 (1984).

Wendoloski et al., "Biophysical Tools for Structure–Based Drug Design" *Pharmacol. Ther.* 60(2), 169–183, (1993).

Weyer, et al., "Human Auto–Anti–Idiotypic Antibodies to Mite–Specific IgE Can Degranulate Human Bastophils in vitro," *Clin. and Exp. All.* 25:935–941, (1995).

Young, et al., "Secretion of Recombinant Human IgE–Fc by Mammalian Cells and Biological Activity of Glycosylation Site Mutants," *Protein Eng.* 8:193–199, (1995).

Yu, et al., "Negative Feedback Regulation of IgE Synthesis by Murine CD23," *Nature* 369: 753–756, (1994).

* cited by examiner

METHODS TO BLOCK IGE BINDING TO CELL SURFACE RECEPTORS OF MAST CELLS

BACKGROUND OF THE INVENTION

The symptoms of allergy in humans and animals are primarily attributable to the release of histamine and a large variety of other bioactive compounds from mast cells and related cell types. The mast cell contains numerous secretary granules in which these substances are stored at extremely high concentrations. Activation of the mast cell results in the fusion of these granules with the cell surface membrane, leading to the exocytosis of the granule contents and the concomitant induction of allergic symptoms. The plasma membrane of these cells are endowed with receptors for the Fc portion of the IgE (FcεRI). This receptor binds circulating IgE with very high affinity and retains it at the mast cell surface for extended periods of time. Activation is accomplished through the binding of an allergen simultaneously to more than one polyvalent molecule of FcεRI-bound IgE. This "cross linking" of at least two surface-bound IgE molecules brings FcεRI proteins into close association with one another in the plane of the mast cell plasma membrane. Kinases associated with these receptors become activated as a result of this proximity, initiating the second messenger cascade which results in cell degranulation.

At least one other class of receptors can bind to the Fc portion of IgE. The low affinity receptor for IgE, FcεRII (also known as CD23) is expressed on mast cells and related cell types, B cells, and subsets of antigen presenting cells. It has been suggested that occupancy of FcεRII negatively regulates IgE synthesis.

It is an object of the present invention to provide a means and method of preventing activation and degranulation of mast cells and related cell types in response to exposure to allergens.

SUMMARY OF THE INVENTION

Compositions are administered to block IgE binding to cell surface receptors and ultimately displace native IgE from mast cells and related cell types to prevent the activation of these cells during an allergic response and to reduce native IgE synthesis. The compositions consist of a pharmaceutically acceptable carrier for systemic or local administration and an amount of compound binding specifically to the FcεRI IgE binding sites, and more preferably, FcεRI and FcεRII IgE binding sites, to prevent activation and degranulation of mast cells in response to exposure to allergens. The compounds can consist of IgE molecules and fragments and modifications thereof, such as IgE fragments, humanized or single chain IgE antibodies or fragments thereof, IgE with a modified Fab, non-crosslinkable IgE, or peptidomimetics which bind to the same site on the receptor as the IgE, jointly referred to herein as "IgE fragments" unless otherwise stated.

DETAILED DESCRIPTION OF THE DISCLOSURE

As used herein, the term "mast cells" includes all cells expressing on their surface FcεRI, including mast cells, basophils, and related cell types.

I. Compounds Specifically Binding to Mast Cell IgE Receptors

IgE Fragments Which Bind to IgE Receptors

Allergen-induced release of mast cell granule contents can be prevented, or minimized, if the FcεRI IgE binding sites in the mast cell plasma membrane are occupied with an analogue of IgE which is unable to bind antigen and thus is incapable of initiating receptor cross-linking. The domain of the IgE protein which binds to its receptor is termed the Fc portion. This component of the IgE molecule does not contain any of the variable regions which contribute to the formation of high affinity antigen binding sites. When the Fc portion of IgE (or selected fragments of the Fc portion) are prepared by enzymatic cleavage or recombinant techniques, the resultant polypeptides bind with high affinity to mast cells. IgE Fc fragments can effectively block the binding of antigen-specific polyvalent native IgE to mast cell FcεRI. Consequently, Fc fragments of the IgE molecule can prevent activation of mast cells by any antigen.

It has been suggested that occupancy of FcεRII negatively regulates IgE synthesis (Yu, et al. Nature 369: 753–756, 1994). Consequently, pharmaceutical administration of IgE fragments is expected to both inhibit binding of native IgE to mast cells and to reduce the secretion of native IgE from patient B cells. To achieve this desirable outcome, it is necessary to administer an IgE fragment which retains the ability to interact with both FcεRI and FcεRII.

Preparation of Recombinant IgE Fc and Modifications to Increase Efficacy

Extensive studies over the previous decade employing proteolysis, site-specific antibodies, chimeric immunoglobulins and recombinant IgE fragments have demonstrated that the Fc portion of the IgE molecule, which is composed of three domains denoted Cε2, Cε3 and Cε4, binds to both FcεRI and FcεRII (Perez-Montfort, R. and H. Metzger. Molec. Immunol. 19:1113–1125, 1982; Rousseaux-Prevost, et al. Molec. Immunol. 24: 187–196, 1987; Burt, et al. Molec. Immunol. 24: 379–389, 1987; Baniyash, et al. Molec. Immunol. 25:705–711, 1988; Weetall, et al. J. Immunol. 145: 3849–3854, 1990; Keegan, et al. Molec. Immunol. 28: 1149–1154, 1991; Moscoso del Prado, et al. Molec. Immunol. 28: 839–844, 1991; Nissim, et al. EMBO J. 10:101–109, 1991; Nissim, A. and Z. Eshhar. Molec. Immunol. 29:1065–1072, 1992; Nissim, et al. J. Immunol. 150: 1365–1374, 1993; Helm, et al., J. Biol. Chem. 271: 7494–7500, 1996; Keown, Eur. Biophys J. 25: 471–476, 1997). The Fc polypeptide can block the binding of IgE to mast cells or basophils in vitro and can block the Prausnitz-Kustner passive sensitization reaction when injected subcutaneously in human subjects (Kenten, et al. Proc. Nat. Acad. Sci. 81:2955–2959, 1984; Coleman, et al. Eur. J.Immunol. 15:966–969, 1985; Geha, et al. Nature. 315:577–578, 1985). The mapping studies demonstrate that the Cε3 region appears to be necessary and sufficient to confer high affinity binding to FcεRI. In contrast, specific association of IgE with FcεRII requires contributions from both the Cε3 and Cε4 domains (Keegan, Molec. Immunol. 28: 1149–1154; 1991; Helm, et al. J. Biol. Chem. 271: 7494–7500, 1996; Vercelli, et al. Nature 338:649–651, 1989). Although a 76 amino acid fragment comprising portions of the Cε2 and Cε3 domains binds to the FcεRI and can inhibit the binding of native IgE in vivo (Helm, et al. Proc. Nat. Acad. Sci. 86:9465–9469, 1989) and in vitro (Helm, et al. Nature 331: 180–183, 1988), the affinity of this molecule for the receptors is approximately ¹⁄₁₀ that of the entire Fc region.

Detailed analysis of the affinities of IgE fragments for FcεRI reveal that the highest affinity is observed with the entire Fc region, which stretches from amino acids 226–547. The on and off rate constants and hence the equilibrium binding constant observed with this piece are essentially identical to the same parameters measured for native IgE (Helm, et al. J. Biol. Chem. 271: 7494–7500, 1996; Keown, et al. Eur. Biophys J. 25: 471–476. 1997). Recombinant IgE fragments can be prepared by expression in *E. coli* (Kenten, et al. Proc. Nat. Acad. Sci. 81:2955–2959, 1984; Coleman, et al. Eur. J.Immunol. 15:966–969, 1985; Ishizaka, et al. Proc. Nat. Acad Sci, 83:8323–8327, 1986; Kurokawa, et al. Nucleic Acids Res. 11:3077–3085, 1983), yeast, insect cells (using a baculovirus system) or in transfected mammalian cells (Ikeyama, Molec. Immunol. 24: 1039–1046, 1987). The protein forms large intracellular inclusion bodies when synthesized in *E. coli*. Following extraction from these inclusion bodies it can be dimerized by oxidative formation of a critical disulfide bond and gains full biological activity (Kenten, et al., 1984; Coleman, et al., 1985). IgE and IgE fragments synthesized in *E. coli* is not glycosylated. Recent evidence indicates that synthesis in mammalian cells of an IgE Fc whose glycosylation sites have been eradicated by site-directed mutagenesis produces a molecule whose affinity for FcεRI is similar to that of native IgE (Young, et al. Protein Eng. 8:193–199, 1995). It would appear, therefore, that lack of glycosylation does not disrupt the FcεRI-binding domain of IgE Fc and that material prepared either in mammalian cells or in *E. coli* should manifest similar biological activities. Furthermore, the non-glycosylated IgE Fc domain exhibits higher affinity binding to the low affinity FcεRII receptor than its fully glycosylated counterpart (Young, et al. Protein Eng. 8:193–199, 1995).

In a preferred embodiment, a cDNA sequence encoding amino acids 226–547 of the human IgE protein which corresponds to the portion of the IgE molecule then is essentially identical to native IgE with respect to its affinity for both the FCεRI and FcεRII receptors (Hehn, et al. J. Biol. Chem. 271: 7494–7500, 1996). Glycosylation sites at Asn 265 and Asn 371 can be removed by site-directed mutagenesis so as to increase the molecule's affinity for FcεRII (Young, et al. Protein Eng. 8:193–199, 1995). Lack of glycosylation should also increase the serum half-life of the circulating molecule, since it will not be a substrate for binding to the asialoglycoprotein receptor (ASGPR), and thus will not be subject to the hepatic clearance and degradation which binding to ASGPR initiates. A potential susceptibility site for cleavage by the serum protease thrombin has been noted in the sequence of the IgE Fc molecule (Kamiya, Human Antibodies and Hybridomas 7:42–47, 1996). This site can be altered by site-directed mutagenesis to ensure that the Fc molecule is not a substrate for thrombin-mediated degradation. By preventing thrombin cleavage and ASGPR-mediated clearance, it should be possible to attain higher levels of circulating IgE fragments for longer periods of time than would be possible with the native molecule. The resultant increase in the serum concentration of IgE fragments will favor the binding of this molecule to the surfaces of patient mast cells and will thus speed the displacement of native IgE required for its therapeutic effects.

It is critically important that the IgE fragments described herein not induce any immune reaction in the patients who receive it. Initiation of a humoral immune response to this molecule would result in the production of polyvalent antibodies which could cross-link the fragments bound to the FcεRI receptors on mast cells surfaces. This cross-linking could, in turn, activate the FcεRI signal cascade and lead to undesirable and potentially catastrophic mast cell degranulation. All of the recombinant IgE Fc fragments described to date have been prepared as fusion proteins. Consequently, they retain protein sequences derived from the fusion construct or from linkers which are not native to the IgE molecule. These sequences are very likely to be immunogenic. Furthermore, the incorporation of N-formyl-methionine at the N-terminus of bacterially synthesized proteins increases the likelihood that IgE fragments generated through bacterial expression will induce an immune response unless post-synthetic modifications are effected. It is unlikely, therefore, that any of the IgE Fc constructs described to date would possess any clinical utility.

These molecules must therefore be designed, or modified, so as to ensure that the sequences described in the preceding paragraph are easily removable to avoid the problems posed by the potential immunogenicity of non-IgE derived sequences. For example, for expression in mammalian, insect or yeast cells, a DNA construct could be employed in which the nucleotide sequence encoding the leader peptide and N-terminal 10 amino acids of rat preprolactin are fused to the sequence corresponding to amino acids 226–547 of IgE Fc. Interposed between the leader peptide sequence and the Fc coding sequence is a sequence encoding a $His_6$ tag followed by a Factor Xa cleavage site. The Fc coding sequence will be inserted immediately 3' to the sequence encoding the Factor Xa cleavage site.

The protein encoded by this cDNA construct will be translated in association with the rough endoplasmic reticulum (RER) and will be co-translationally transported across the RER membrane with concomitant cleavage of the leader peptide. The protein will pursue the secretory pathway and can be released constitutively from the cells. Metal ion chromatography can be used to recover the secreted His-tagged protein from the culture media. Cleavage with Factor Xa will generate a protein whose N-terminal amino acid residue corresponds to amino acid 226 of the IgE Fc protein sequence. Cleaved protein will be purified by gel filtration chromatography.

A similar approach can be taken for bacterial expression. A methionine start codon will follow the promoter sequence, after which will be inserted the $His_6$ tag and the Factor Xa cleavage site. Bacterially synthesized protein will be recovered from the inclusion bodies, purified by metal ion chromatography, cleaved by Factor Xa and dimerized through oxidation. Once again, the N-terminal residue will correspond to amino acid 226 of the IgE Fc sequence. Intact dimer will be prepared by gel filtration chromatography. The vectors employed to drive synthesis in mammalian, insect or yeast cells or in bacteria will incorporate promoters designed to maximize exogenous protein expression.

Humanization of Antibodies

The IgE used to prepare the analogs can be human or animal, and will typically be animal if monoclonal antibodies are used as a source. Since the methods for immunizing animals yield antibody which is not of human origin, the antibodies could elicit an adverse effect if administered to humans. This is also true if the antibodies are to be administered to any other species which is different from the species of origin of the antibodies. As used herein, "humanization" refers to modifying the species-specific region of the antibody to be homologous to the species to be treated. Methods for "humanizing" antibodies, or generating less immunogenic fragments of non-human antibodies, are well known. A humanized antibody is one in which only the antigen-recognized sites, or complementarity-determining hypervariable regions (CDRs) are of non-human origin, whereas all framework regions (FR) of variable domains are products of human genes. These "humanized" antibodies present a less xenografic rejection stimulus when introduced to a human recipient.

To accomplish humanization of a selected mouse monoclonal antibody, the CDR grafting method described by Daugherty, et al., *Nucl. Acids Res.*, 19:2471–2476 (1991) may be used. Briefly, the variable region DNA of a selected animal recombinant anti-idiotypic ScFv is sequenced by the method of Clackson, T., et al., *Nature*, 352:624–688, 1991. Using this sequence, animal CDRs are distinguished from animal framework regions (FR) based on locations of the CDRs in known sequences of animal variable genes. Kabat, H. A., et al., Sequences of Proteins of Immunological Interest, 4th Ed. (U.S. Dept. Health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The immunogenic stimulus presented by the monoclonal antibodies so produced may be further decreased by the use of Pharmacia's (Pharmacia LKB Biotechnology, Sweden) "Recombinant Phage Antibody System" (RPAS), which generates a single-chain Fv fragment (ScFv) which incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Compared to the intact monoclonal antibody, the recombinant ScFv includes a considerably lower number of epitopes, and thereby presents a much weaker immunogenic stimulus when injected into humans.

Compounds Identified by Combinatorial Chemistry

It may be preferable to utilize non-peptide compounds to block binding of IgE to the mast cell receptors. Molecules with a given function, for example, binding, can be selected for from a complex mixture of random molecules in what has been referred to as "in vitro genetics" (Szostak, *TIBS* 19:89, 1992) or combinatorial chemistry. One synthesizes a large pool of molecules bearing random and defined sequences and subjects that complex mixture, for example, approximately $10^{15}$ individual sequences in 100 $\mu$g of a 100 nucleotide RNA or DNA, to some selection and enrichment process. For example, by repeated cycles of affinity chromatography and PCR amplification of the molecules bound to the ligand on the column, Ellington and Szostak (1990) estimated that 1 in $10^{10}$ RNA molecules folded in such a way as to bind a given ligand. DNA molecules with binding behavior have also been isolated (Ellington and Szostak, 1992; Bock et al, 1992).

Using methodology well known to those of skill in the art, in combination with various combinatorial libraries, one can isolate and characterize those compounds which bind to or interact with the desired target. The relative binding affinity of these compounds can be compared and optimum compounds identified using competitive binding studies which are well known to those of skill in the art.

For example, the mast cell receptor(s), or relevant portions thereof, can be bound to a solid support, and interacted with various combinatorial libraries. Those molecules which do not bind these molecules at all are removed immediately by elution with a suitable solvent. Those molecules which bind to inactive portions of the receptor(s) can be removed by competitive binding with an excess of a chimeric peptide with the inactive portions represented by human sequences, or sequences from the desired species, and the active portion represented by the sequence from another species. Those compounds which bind to the receptor(s) will remain bound to the solid support, whereas unbound compounds will be removed from the column. Finally, those compounds still bound to the column can be removed, for example, by competitive binding. Following removal, these compounds can be identified and their relative binding affinity compared as described above.

Rational Drug Design

Drugs with the ability to mimic the function of the portion of the IgE which binds to the mast cell receptors can be identified using rational drug design. The compounds preferably include the surface active functional groups of the IgE, or substantially similar groups, in the same or substantially similar orientation, so that the compounds possess the same or similar biological activity. The surface active functional groups in the IgE possess a certain orientation when they are in their active conformations, in part due to their secondary or tertiary structure. Rational drug design involves both the identification and chemical modification of suitable compounds which mimic the function of the parent molecules.

Compounds that mimic the conformation and desirable features of a particular peptide, e.g., an oligopeptide, but that avoid undesirable features, e.g., flexibility (loss of conformation) and metabolic degradation, are known as "peptidomimetics". Peptidomimetics that have physical conformations which mimic the three dimensional structure of amino acids 226–547 of the human IgE protein, in particular, which have surface active groups as present in this portion of the IgE, or peptidomimetics that have physical conformations which mimic the three dimensional structure of amino acids amino acids 226–547 of the human IgE protein can be used to make the pharmaceutical compositions described herein.

The physical conformation of the peptidomimetics are determined, in part, by their primary, secondary and tertiary structure. The primary structure of a peptide is defined by the number and precise sequence of amino acids in the IgE. The secondary structure is defined by the extent to which the polypeptide chains possess any helical or other stable structure. The tertiary structure is defined by the tendency for the polypeptides to undergo extensive coiling or folding to produce a complex, somewhat rigid three-dimensional structure.

Computer modeling technology allows visualization of the three-dimensional atomic structure of a selected molecule and the rational design of new compounds which will mimic the molecule or which will interact with the molecule. The three-dimensional structure can be determined based on data from x-ray crystallographic analyses and/or NMR imaging of the selected molecule, or from ab initio techniques based solely or in part on the primary structure, as described, for example, in U.S. Pat. No. 5,612,895 to Balaji et al. The computer graphics systems enable one to predict how a new compound will link to the target molecule and allow experimental manipulation of the structures of the compound and target molecule to perfect binding specificity.

Many databases and computer software programs are known that can be used to design drugs. For example, see Ghoshal et al., "Computer Aids in Drug Design—Highlights" (1996) *Pol. J. Pharmacol.* 48(4), 359–377; Wendoloski et al., "Biophysical Tools for Structure-Based Drug Design" (1993) *Pharmacol. Ther.* 60(2), 169–183; Lybrand, "Ligand-Protein Docking and Rational Drug Design" (1995) *Curr. Opin. Struct. Biol.* 5(2), 224–228; Kleinberg and Wanke, "New Approaches and Technologies in Drug Design and Discovery" (1995) *Am. J. Health Syst. Pharm.* 52(12), 1323–1336; Kubinyi, "Strategies and Recent Technologies in Drug Discovery" (1995) *Pharmazie* 50(10), 647–662; Archakov et al., (1996) *Vestn. Ross. Akad. Med. Nauk.* 1, 60–63; Taylor and Smith, "The Word Wide Web as a Graphical User Interface to Program Macros for Molecular Graphics, Molecular Modeling, and Structure-Based Drug Design" (1996) *J. Mol. Graph.* 14(5), 291–296; Huang et al., "Development of a Common 3D Pharmacophore for Delta-Opioid Recognition From Peptides and Non-Peptides Using a Novel Computer Program" (1997) *J. Comput. Aided Mol. Des.* 11(1), 21–78; and Li et al., "A computer Screening Approach to Imnmunoglobulin Superfamily Structures and Interactions: Discovery of Small Non-Peptidic CD4 Inhibitors and Novel Immunotherapeutics (1997) *Proc. Natl. Acad. Sci. USA* 94(1), 73–78.

Data bases including constrained metabolically stable non-peptide moieties may be used to search for and to suggest suitable IgE analogs. Searches can be performed using a three dimensional data base for non-peptide (organic) structures (e.g., non-peptide analogs, and/or dipeptide analogs) having three dimensional similarity to the known structure of the active regions of these molecules. See, e.g., the Cambridge Crystal Structure Data Base, Crystallographic Data Center, Lensfield Road, Cambridge, CB2 1EW, England; and Allen, F. H., et al., *Acta Crystallogr.,* B35: 2331–2339 (1979). Alternatively, three dimensional structures generated by other means such as molecular mechanics can be consulted. See., e.g., Burkert, et al., *Molecular Mechanics*, American Chemical Society, Washington, D.C. (1982); and Weiner, et al., *J. Am. Chem. Soc.*, 106(3): 765–84 (Eng.) (1984).

Search algorithms for three dimensional data base comparisons are available in the literature. See, e.g., Cooper, et al., *J. Comput.-Aided Mol. Design,* 3: 253–259 (1989) and references cited therein; Brent, et al., *J. Comput.-Aided Mol. Design,* 2: 311–310 (1988) and references cited therein. Commercial software for such searches is also available from vendors such as Day Light Information Systems, Inc., Irvine, Calif. 92714, and Molecular Design Limited, 2132 Faralton Drive, San Leandro, Calif. 94577. The searching is done in a systematic fashion by simulating or synthesizing analogs having a substitute moiety at every residue level. Preferably, care is taken that replacement of portions of the backbone does not disturb the tertiary structure and that the side chain substitutions are compatible to retain the IgE/receptor interactions. Using the information regarding bond angles and spatial geometry of the critical amino acids, one can use computer programs as described herein to develop peptidomimetics.

Chemical Modifications

Chemically modified analogs of the active portion of the IgE fragment can also be identified using the techniques described above. Peptidomimetics can be modified to increase bioavailability. Preferably, the compounds are structurally constrained such that the surface active groups are oriented in the active conformation. The compounds can further include chemical modifications that minimize the metabolic degradation of the compounds once they are administered. See, for example, Spatola, A. F. *Chemistry and Biochemistry of Amino Acids, Peptides, and Proteins* (Weistein, B, Ed.), Vol. 7, pp. 257–357, Marcel Dekker, New York (1983), which describes the use of the methylenethio bioisostere [$CH_2S$] as an amide replacement; and Szelke et al., *In Peptides: Structure and Function, Proceedings of the Eighth American Peptide Symposium,* (Hruby and Rich, Eds.); pp. 579–582, Pierce Chemical Co., Rockford, Ill. (1983), which describes methyleneamino [$CH_2NH$] and hydroxyethylene [$CHOHCH_2$] bioisosteres.

The flexible portions of the structure can be replaced with suitable bioisosteres or equivalents, so that the active conformation can be maintained. As defined herein, the term "bioisostere" refers to atoms or groups of atoms which are of similar size to the atom or group of atoms which are to be replaced, wherein the compound containing the replacement atom or group of atoms retains, to a substantial degree, the biological activity of the original, unmodified peptide. See, for example, Nelson, Mautner, and Kuntz, at pp. 227, 271 and 285, respectively, in *Burger's Medicinal Chemistry*, Part 1, the Basis of Medicinal Chemistry, 4th Edition, M. E. Wolff, ed. (John Wiley & Sons, New York, 1980).

Numerous peptide backbone substitutions are known to those of skill in the art which can provide peptidomimetics with improved physical and chemical properties, including enhanced rigidity and chemical and/or metabolic stability. Suitable substitutions include modifying one or more of the amide bonds by replacing the amide nitrogen with an oxygen atom, or a sulfur atom, or by replacing H at the amide nitrogen with an alkyl, aryl, aralkyl or alkaryl group, producing an N-substituted amide, or by replacing the amide group with a methylene moiety, optionally substituted with one or two alkyl, aryl, aralkyl or alkaryl groups, which can in turn optionally be substituted with various functional groups, such as halogens, carbonyl groups, amines, nitrites, azides, thiols, hydroxy groups, and carboxylic acid groups. The alkyl groups are preferably $C_{1-6}$ straight, branched or cyclic groups. Further, one or more of the amide bonds present in the peptide backbone can be modified, for example, by replacing the amide carbonyl group with a methylene group (optionally substituted as described above), a thiocarbonyl group, a sulfone moiety or a sulfoxide moiety.

The peptide can be further modified by introducing alkyl, aryl, aralkyl or alkaryl substituents, optionally substituted as described above, at one or more of the alpha-carbon atoms, such that the peptide backbone is unchanged, but additional side chain substituents are present in the chemically modified analog. Suitable α-carbon atom modifications include cyclopropyl groups, ethylidene groups, and primary, secondary or tertiary amines.

Each of these modifications can be introduced into the peptide chain in either orientation (i.e., in the orientation shown, or in the "reverse" orientation). In addition, various substituents on the amide nitrogen and the α-carbon can be bound to one another, thereby forming a cyclic structure which is a relatively constrained analog. Other constrained, cyclic structures can also be prepared by linking various substituents to form cyclic structures using chemical techniques know to those of skill in the art. Other modifications include those described in U.S. Pat. No. 5,612,895 to Balaji et el., the contents of which are hereby incorporated by reference.

Chemically modified analogs are typically more resistant to enzymatic cleavage than the native peptides from which they are derived because the modified residues are not typically recognized by the enzymes which degrade naturally occurring proteins. Further, the backbone and side chains of peptides can be modified to provide peptidomimetics with reduced conformational flexibility. Accordingly, the possibility that the peptide will adopt conformation(s)

other than the specifically desired conformation(s) can be substantially minimized by appropriate modification.

Methods of Chemically Preparing IgE Analogs

Once the desired analog (including backbone and side chain modifications, as appropriate) has been identified, chemical synthesis is undertaken, employing standard synthetic techniques. For a given target compound, the skilled artisan can readily identify suitable synthetic approaches for the preparation of the target compound. Particular techniques for synthesizing certain classes of compounds are described in more detail below.

Proteins can be expressed recombinantly or naturally and cleaved by enzymatic digest, expressed from a sequence encoding just a peptide, or synthesized using standard techniques. It is a routine matter to make appropriate peptides, test for binding, and then utilize the peptides. The peptides are easily prepared by standard techniques. They can also be modified to increase in vivo half-life, by chemical modification of the amino acids or by attachment to a carrier molecule or inert substrate, as discussed above. The peptides can also be conjugated to a carrier protein by standard procedures such as the commercial Imject ™ kit from Pierce Chemicals or expressed as a fusion protein, which may have increased stability. Solid phase synthesis described by J. Merrifield, 1964 *J. Am. Chem. Soc.* 85, 2149, used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305,872 and 4,316,891, the contents of which are hereby incorporated by reference. These methods can be used to synthesize peptides having identical sequence to the receptor proteins described herein, or substitutions or additions of amino acids, which can be screened for activity as described above.

The peptide can also be prepared as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Peptides containing cyclopropyl amino acids, or amino acids derivatized in a similar fashion, can also be used. These peptides retain their original activity but have increased half-lives in vivo. Methods known for modifying amino acids, and their use, are known to those skilled in the art, for example, as described in U.S. Pat. No 4,629,784 to Stammer.

After the compounds are synthesized, their biological activity can be evaluated, for example, using competitive binding studies, and iterative refinement of the peptidomimetic (in the case of a constrained analog itself) can then be carried out. Those chemically modified analogs which are biologically active can be employed as peptidomimetics without further modification.

II. Pharmaceutical Compositions

Formulations

Dissociation of IgE from its receptor is extremely slow, exhibiting half-times of days to weeks (Isersky, et al. J. Immunol. 122: 1926–1936, 1979). Consequently, IgE fragments bound to FcεRI should produce a stable and long term block of these receptors' capacity to activate mast cells. It must also be noted, however, that in order to be effective, IgE fragments will need to occupy a sufficient number of receptor to block antigen-induced activation of the mast cells. Thus, any pharmaceutical preparation of IgE fragments must be presented in sufficiently high concentration and for a sufficient length of time to displace native IgE from the patient's mast cell population.

The compounds described above are preferably administered in a pharmaceutically acceptable vehicle. Suitable pharmaceutical vehicles are known to those skilled in the art. For parenteral administration, the compound will usually be dissolved or suspended in sterile water or saline. Carriers suitable for local release, including administration by inhalation or by injection into muscle for production of recombinant IgE by the individual to be treated, or topical administration, include ointments, salves, lotions, gels, and controlled release formulations, such as liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214.

The formulation and method for administration can be used to modulate the specific IgE responses. For example, as described by Vrtala, et al., *Int. Arch. Allergy Immunol.* 107(1-3), 290–294 (1995), an antigen can be administered to an individual through the use of a recombinant expression host, such as an apathogenic Salmonella strain, which can be orally administered. Studies by Vrtala, et al., showed that this method induced a Th1 immune response with undetectable IgG1 or IgE.

Methods for Administration

One of the following four routes of administration to achieve the daily dosage calculated below for the required period of time.

A. Direct subcutaneous injection.

B. Implantation of a subcutaneous depot.

C. Direct injection into a muscle of cDNA vector encoding the requisite portion of IgE fragments under the control of a strong muscle-specific promoter. Similar techniques have been employed to express factor VII in mice (Miller, et al. Gene Therapy 2: 736–742, 1995). To ensure that expression of the exogenous gene could be discontinued in the event that it proved to be deleterious, IgE fragments coding sequence would be flanked by lox sequences. The sequence encoding the CRE recombinase would also be carried by the vector, under the control of a tight inducible promoter. Activation of the inducible promoter through ingestion of a small molecule (i.e., tetracycline) would activate the CRE recombinase, leading to the excision of the lox-flanked IgE fragments sequence (Tsien, et al. Cell 87:1317–1326, 1996). Similarly, transfected MHC-matched cells expressing and secreting IgE fragments could be infused or implanted. Co-transfection of these cells with the cDNA encoding the Herpes Simplex Virus thymidine kinase would ensure that they could be killed through the administration of acyclovir, should the need to eliminate them arise (Bonin, et al. Science 276: 1719–1724, 1997).

D. Numerous studies demonstrate that the pulmonary epithelium is permeable to fairly large proteins (Gensch, et al. Science 157:1204–10206, 1967). The therapeutic potential of pulmonary administration of intact proteins has been demonstrated for insulin (Elliot, et al. Aust. Paediatr. J. 23: 293–297, 1987) and is being explored for human growth hormone (Patton, et al. Biotech. Therap. 1:213–228, 1990). The serum levels attainable through pulmonary administration are comparable to those which can be achieved through parenteral administration (Patton, et al. Biotech. Therap. 1:213–228, 1990). It is likely, therefore, that sufficiently high plasma levels of IgE fragments could be achieved through inhalation-based pulmonary administration. It is also important to note that a very large proportion of allergy symptoms are attributable to the degranulation of mast cells embedded within the nasal and pulmonary epithelium. Furthermore, recent evidence indicates that the IgE responsible for the nasal symptoms of allergy is synthesized locally within the nose itself (Durham, et al. Eur. J. Immunol. 27: 2899–2906, 1997; Durham, et al. Int. Arch. of Allergy and Immunol. 113: 128–130, 1997). Inhalation might be expected to deliver extremely high concentrations IgE fragments directly to this important population of nasal and respiratory mast cells. Inhibition of allergen-induced degranulation of nasal and pulmonary mast cells might be expected to dramatically ameliorate symptoms such as allergic rhintis and bronchiolar constriction. Thus, even if the circulating levels of IgE fragments which can be achieved by inhalation are not sufficient to ensure that mast cells throughout the entire system are disarmed, the local inactivation of pulmonary and nasal mast cells might be sufficient to bring about significant symptomatic relief. It is likely, therefore, that the dose of IgE fragment required to bring about relief of nasal and respiratory allergic symptoms will be much smaller (and hence more easily attainable and maintainable) than that required for the systemic dose calculated below.

Dosages

In the preferred embodiment, pharmaceutically acceptable carriers will typically by saline, phosphate buffered saline, or water, if the composition is administered by injection. The pharmaceutical preparation of the human IgE fragment, or analogue, is administered for the dual purposes of occupying mast cell FcεRI receptors so as to prevent allergen-induced degranulation and occupying FcεRII receptors to reduce circulating levels of native IgE. This preparation serves as a pan-specific anti-allergy therapy, relieving and preventing allergy symptoms independent of the nature of the allergen. Consequently, patients allergic to multiple substances will be completely treated by this preparation, obviating the need for multiple courses of allergen-specific immunizations.

Previous animal studies indicate that systemic delivery of approximately 25 mg/kg/day of monospecific IgE is sufficient to block subsequent passive sensitization with a different monospecific IgE (Spiegelberg, et al. J. Immunol. 136:131–135, 1986). However, this dose of IgE delivered daily over 13 days did not significantly diminish the allergic response in animals which had been actively immunized with a specific allergen on day 0 or −3 of the protocol. Given the extremely long half-life of IgE bound to FcεRI at the mast cell surface (Isersky, et al. J. Immunol. 122: 1926–1936, 1979), this observation is not at all surprising. To attain therapeutic levels of displacement of native IgE from patient mast cells it will be necessary to maintain continuously high circulating levels of exogenous IgE fragments for at least 6–8 weeks. Serum IgE concentrations in adults are approximately $10^{-8}$ g/ml (Nye, et al. Clin. Allergy 1:13–24; 1975). It is desirable, therefore, to maintain continuous serum IgE fragments concentrations of at least $5 \times 10^{-6}$ g/ml. A similar 100-fold excess was sufficient to block the Prausnitz-Kustner passive immunication reaction in human subjects (Geha, et al. Nature. 315:577–578, 1985). Since the half-life of circulating IgE is approximately 12 hours (Spiegelberg, et al. J. Immunol. 136:131–135, 1986), between approximately 0.4 and 0.8 G should constitute a reasonable upper estimate of the single daily dose required for a 70 kg individual.

IV. Assays for Efficacy

Serum levels of IgE fragments can be measured by quantitative western blot analysis employing an $[^{125}I]$-conjugated anti-IgE fragments antibody as a probe. Protein in serum samples is separated by SDS polyacrylamide gel electrophoresis (SDS-PAGE) followed by electrophoretic transfer to nitroclluose paper. For quantitation purposes, a dilution series of known quantities of IgE is also to be loaded on separate lanes of the same gel. IgE fragments can be distinguished from native IgE by its distinctive molecular weight. Labelled bands are excised and bound radioactivity determined by γ-counting.

Fractional levels of IgE fragments bound to FcεRI can be determined by quantitative western blotting. Peripheral blood basophils can be isolated from patient serum (Weyer, et al. Clin. and Exp. All. 25:935–941, 1995) and their associated proteins separated by SDS-PAGE followed by electrophoretic transfer. The relative quantity of native IgE versus IgE fragments bound to the cells is determined using quantitative western blot analysis employing an $[^{125}I]$-conjugated anti-IGE fragments antibody as a probe. Native IgE is distinguished from IgE fragments by virtue of their distinct molecular weights. Radioactivity in excised bands can be quantitated by γ-counting and the native IgE/IgE fragments ratio determined.

The susceptibility of cells from treated patients to undergo cross-linking dependent granule exocytosis can be determined with peripheral blood basophils, prepared from patient serum (Weyer, et al. Clin. and Exp. All. 25:935–941, 1995). Cells can be exposed to a bivalent IgG antibody directed against the Fab portion of IgE. This reagent should not interact with surface-bound IgE fragment. Degranulation is measured by standard techniques (Weyer, et al. 1995). This treatment should not induce basophils from successfully treated patients to degranulate. An IgG antibody directed against the Fc portion of IgE is employed as a positive control to demonstrate that the basophils from treated patients retain the capacity to undergo cross-linking mediated degranulation.

Modifications and variations of the present invention will be obvious to those skilled in the art. Such modifications and variations are intended to come within the scope of the invention.

We claim:

1. A method of inhibiting an allergic response comprising administering to an individual in need thereof an effective amount of a composition that prevents clinically significant allergen-induced mast cell activation, which composition comprises a pharmaceutically acceptable carrier; and a compound that binds to the IgE binding site of an Fcε receptor to prevent occupancy of the receptor by native IgE, which compound cannot be cross-linked by antigen, and does not elicit an immune reaction, wherein the composition is administered in a dosage effective to maintain a serum concentration of the compound equivalent to at least $5 \times 10^{-6}$ g IgE fragments/ml or a dosage equivalent to between 0.4 and 0.8 g IgE fragments/70 kg person/day, and wherein the composition is administered for a period of time of at least one month effective to displace native IgE from the individual's mast cells.

2. The method of claim 1 wherein the compounds are selected from the group of compounds binding to the FcεRI on mast cells consisting of human IgE fragments, recombinant IgE fragments, and single chain IgE fragments.

3. The method of claim 1 wherein the compounds are non-crosslinkable recombinant antibodies to FcεRI.

4. The method of claim 1 wherein the compound is a peptidominetic.

5. The method of claim 1 wherein the composition is administered to the individual in need thereof by injection.

6. The method of claim 1 wherein the composition is administered to the individual in need thereof by inhalation.

7. The method of claim 1 wherein the composition is administered to the individual in need thereof locally or topically.

8. The method of claim 1 formulated for controlled release.

9. The method of claim 1 formulated to maximize mucosal adhesion and release.

10. The method of claim 1 wherein the compound is administered for at least six weeks.

11. The method of claim 1 wherein the compound is administered systemically.

* * * * *